United States Patent [19]

Shinohara et al.

[11] 4,371,524

[45] * Feb. 1, 1983

[54] ANTICOMPLEMENTARY AGENTS COMPRISING SOYASAPOGENOL B COMPOUNDS

[75] Inventors: Masanao Shinohara, Naruto; Yoshimasa Nakano, Tokushima; Hirotsugu Kaise, Tokushima; Taketoshi Izawa, Tokushima; Wasei Miyazaki, Tokushima, all of Japan

[73] Assignee: Otsuka Pharmaceutical Co., Ltd., Tokyo, Japan

[*] Notice: The portion of the term of this patent subsequent to Aug. 12, 1997, has been disclaimed.

[21] Appl. No.: 241,294

[22] Filed: Mar. 6, 1981

Related U.S. Application Data

[63] Continuation of Ser. No. 25,517, Mar. 30, 1979, abandoned.

[30] Foreign Application Priority Data

Mar. 31, 1978 [JP] Japan ............................ 53-38536
May 17, 1978 [JP] Japan ............................ 53-59345

[51] Int. Cl.³ ............................................. A61K 31/70
[52] U.S. Cl. ..................................................... 424/180
[58] Field of Search ................ 536/4, 17; 424/180, 424/182

[56] References Cited

FOREIGN PATENT DOCUMENTS 52-83958 7/1977 Japan .

OTHER PUBLICATIONS

Kitagawa, I., et al., Chem. Pharm. Bull., vol. 24, pp. 121–129, 1976.
Kitagawa, I., et al., Chem. Pharm. Bull., vol. 22, pp. 3013–3015, 1974.

*Primary Examiner*—Blondel Hazel
*Attorney, Agent, or Firm*—Sughrue, Mion, Zinn, Macpeak & Seas

[57] ABSTRACT

A pharmaceutical composition having an anticomplementary activity comprising a therapeutically effective amount of at least one soyasapogenol B compound represented by the general formula (I):

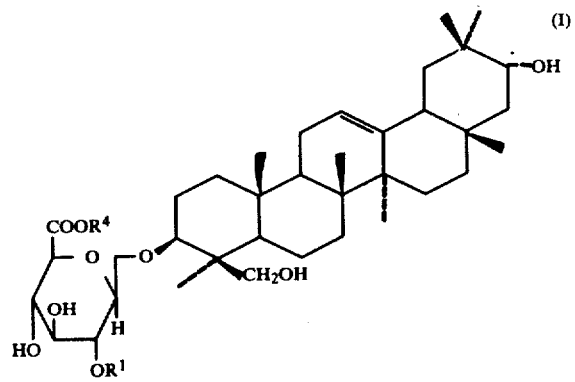

wherein $R^1$ represents a hydrogen atom or a group represented by the formula:

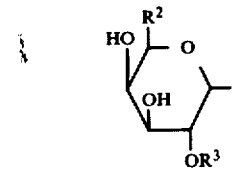

wherein $R^2$ represents a hydrogen atom or a hydroxymethyl group, $R^3$ represents a hydrogen atom or a rhamnopyranosyl group, and $R^4$ represents a hydrogen atom or an alkyl group having 1 to 6 carbon atoms or pharmaceutically acceptable salts thereof and a pharmaceutically acceptable carrier.

7 Claims, No Drawings

ANTICOMPLEMENTARY AGENTS COMPRISING SOYASAPOGENOL B COMPOUNDS

This is a continuation of application Ser. No. 25,517, filed Mar. 30, 1979, now abandoned.

BACKGROUND OF THE INVENTION

1. Field of the Invention

This invention relates to anticomplementary agents comprising as the active ingredient at least one soyasapogenol B compound represented by the general formula (I):

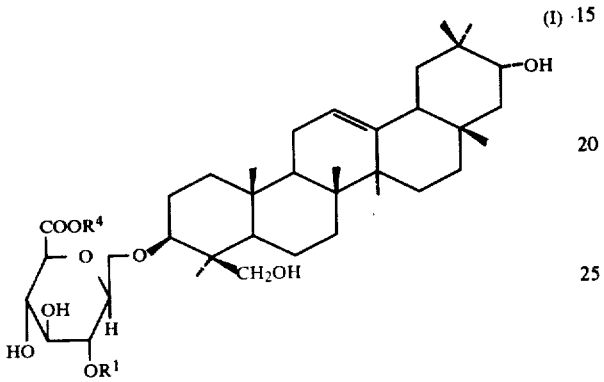

wherein $R^1$ represents a hydrogen atom or a group represented by the formula:

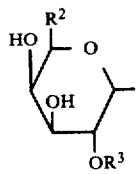

wherein $R^2$ represents a hydrogen atom or a hydroxymethyl group, $R^3$ represents a hydrogen atom or a rhamnopyranosyl group, and $R^4$ represents a hydrogen atom or an alkyl group having 1 to 6 carbon atoms and pharmaceutically acceptable salts thereof.

This invention also relates to a process for preparing anticomplementary agents comprising the compound of the formul (I) or pharmaceutically acceptable salts thereof as the active ingredient.

Further, this invention relates to a process for treating nephritis. 2. Description of the Prior Art Various compounds related to the active ingredients of the anticomplementary agents of this invention are known. For example, glycyrrhizin (Yasuhiro Ariga, Hiroyuki Sumi, Yumiko Takada and Akikazu Takada, *Abridgements of Lecture Programs on Seminar of Plasmin Research Association*, page 65 (1977); Koretsugu Arimoto, Kaneyuki Mineta, Hiroyuki Sumi, Yumiko Takada and Akikazu Takada, *Proceedings of the 14th Symposium on Complements*, pp. 79–82 (1977)) and 3-O-(6-O-methylβ-D-glucuronopyranosyl)-soyasapogenol B (Isao Kitagawa, Masayuki Yoshikawa and Ichiro Yoshioka, *Chem. Pharm. Bull.*, 22, p, 1339 (1974); Ibid., 24, p. 121 (1976)), etc., are known. The former compound has a steroid like structure and exhibits an activity similar to that of steroids. For example, it shows an inhibitory activity against plasmin, urokinase, Kallikrein, thrombin and complements. On the other hand, the physiological activities of the latter have not yet been reported. In contrast, the compounds of the formula (I) and salts thereof used in the agents of this invention have an anticomplementary activity which is unexpectedly superior to that of glycyrrhizin and which is quite unexpected from 3-0-(6-0-methyl-β-D-glucuronopyranosyl)-soyasapogenol B as will be apparent from the results of pharmacological tests described hereinafter.

SUMMARY OF THE INVENTION

An object of this invention is to provide potent anticomplementary agents which comprise soyasapogenol B compounds or pharmaceutically acceptable salts thereof.

Another object of this invention is to provide a process for preparing such anticomplementary agents.

Still another object of this invention is to provide a process for treating nephritis using such anticomplementary agents.

This invention provides pharmaceutical compositions containing a therapeutically effective amount of the soyasapogenol B derivative of the formula (I) above or pharmaceutically acceptable salts thereof for achieving anticomplementary activity in animals and a method of use, particularly treating nephritic disorders in animals, comprising administering the pharmaceutical composition to a patient afflicted with such a disorder.

DETAILED DESCRIPTION OF THE INVENTION

The anticomplementary pharmaceutical compositions of this invention may be used to relieve or prevent pathological reactions requiring the function of a complement and in the therapeutic treatment of immunologic diseases such as rheumatoid arthritis, systemic lupus erythematosus, glomerulonephritis, autoallergic hemolytic anemia, platelet disorders, vasculitis, etc. The pharmaceutical compositions of this invention may also be used in the therapeutic treatment of non-immunologic diseases such as paroxyamal nocturnal hemoglobinuria, hereditary angioneurotic edema and inflammatory states induced by the action of bacterial or lysosomal enzymes on the appropriate complement components as, for example, inflammation following coronary occlusion. They may also be useful in the treatment of transplant rejections and as blood culture and transport mediums. Further, they may be used in the therapeutic treatment of disseminated intravascular coagulation.

In recent years, extensive research has been made on the theoretical analysis of the complement system and its effects on humans and animals and at present it is generally recognized that when certain compounds have an anticomplementary activity they can exhibit therapeutic effects on various symptoms described above. For example, U.S. Pat. No. 4,021,544 discloses the following.

"The term 'complement' refers to a complex group of proteins in body fluids that, working together with antibodies or other factors, play an important role as mediators of immune, allergic, immunochemical and/or immunopathological reactions. The reactions in which a complement participates take place in blood serum or in other body fluids, and hence are considered to be humoral reactions."

"With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935–938 (1968), *Scientific American*, 229, (No. 5), 54–66 (1973), *Medical World News*, Oct. 11, 1974, pp. 53–58, 64–66, *Harvey Lectures*, 66, 75–104 (1972); *The New England Journal of Medicine*, 287, 489–495, 545–549, 592–596, 642–646 (1972); *The John Hopkins Med. J.*, 128, 57–74 (1971), and *Federation Proceeding*, 32, 134–137 (1973)."

"The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and, (3) an attack unit (C5, C6, C7, C8 and C9) which creates a hole in the membrane. The membrane attack unit is nonspecific; it destroys invaders only because it is generated in their neighborhood in order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword."

"Activation of the complement system also accelerates blood clotting. This action comes about by way of the complement-mediated release of a clotting factor from platelets. The biologically active complement fragment and complexes can become involved in reactions that damage the host's cells, and these pathogenic reactions can result in the development of immune-complex diseases. For example, in some forms of nephritis the complement damages the basal membrane of the kidney, resulting in the escape of protein from the blood into the urine. The disease disseminated lupus erythematosus belongs in this catetory; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune-complexes. Like disseminated lupus erythematosus, it is an autoimmune disease. in which the disease symptoms are caused by pathological effects of the immume system in the host's tissues. In summary, the complement system has been shown to be involved with inflammation, coagulation, fibrinolysis, antibody-antigen reactions and other metabolic processes."

"In the presence of antibody-antigen complexes the complement proteins are involved in a series of reactions which may lead to irreversible membrane damage if they occur in the vicinity of biological membranes. Thus, while the complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969)."

"It has been reported that the known complement inhibitors, epsilon-aminocaproic acid, Suramin Sodium and tranexamic acid, have been used with success in the treatment of hereditary angioneurotic edema, a disease state resulting from an inherited deficiency or lack of function of the serum inhibitor of the activated first component of the complement (C1 inhibitor), *The New England Journal of Medicine*, 286, 808–812 (1972); *Allergol*, Et. *Immunipath*, II, 163–168 (1974); *J. Allergy Clin. Immunol*, 53, No. 5, 298–302 (1974); and *Annals of Internal Medicine*, 84, 580–593 (1976)."

Some of the soyasapogenol derivatives of the formula (I) above are known whereas others are new. The alkyl group represented by $R^4$ or $R^{4'}$ (in the formula (Ia) below) includes linear or branched alkyl groups having 1 to 6 carbon atoms such as a methyl group, an ethyl group, a propyl group, an isopropyl group, a butyl group, a tert-butyl group, a pentyl group, a hexyl group, etc.

The compounds of the formula (I) above can be prepared in various manners. For example, the compound represented by the formula (I) can be prepared by first separating soyasaponin B from soybeans and then treating this compound in accordance with Reaction Scheme-1 described hereinafter.

The separation of soyasaponin B can be carried out using known separating processes and means. Examples of suitable chemical treatments include hydrolysis, alcoholysis, etherification, acylation, etc. Examples of suitable physical treatments include solvent extraction, solvent dilution, liquid chromatography, gas chromatography, recrystallization, etc.

More specifically, the compound represented by the formula (I) can be prepared by subjecting soyasaponin B obtained in accordance with the process of Kitagawa et al (Isao Kitagawa, Masayuki Yoshikawa and Ichiro Yoshioka, *Chem. Pharm. Bull.*, 22, p. 1339 (1974), Ibid., 24, p. 121 (1976)) to alcoholysis with a lower alcohol such as methanol, ethanol, propanol, isopropanol, butanol, pentanol, hexanol, etc., in the presence of an acid to form 3-0-(6-0-alkyl-$\beta$-D-glucuronopyranosyl)-soyasapogenol B and then hydrolyzing it (Reaction Scheme-1).

The term "soyasapogenol B" as used herein refers to a mixture of soyasanins I, II and III which contain soyasapogenol B as an aglycon as described in the above-mentioned literature references.

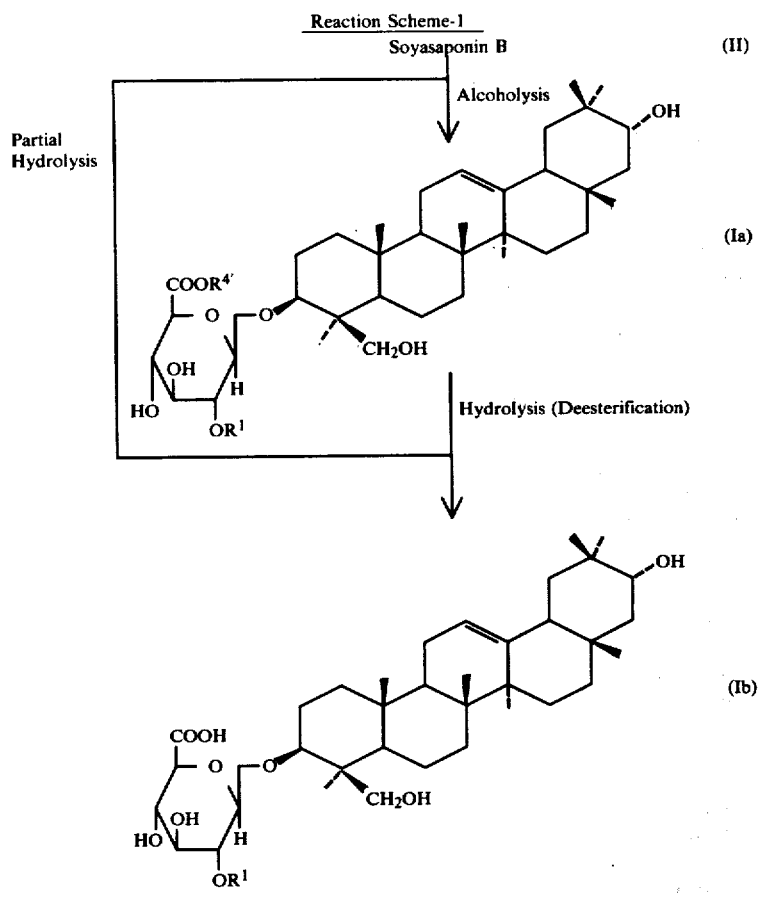

Reaction Scheme-1

In the above formulae (Ia) and (Ib), $R^1$ represent a hydrogen atom or a group represented by the formula:

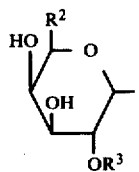

where $R^2$ represents a hydrogen atom or a hydroxymethyl group, $R^3$ represents a hydrogen atom or a rhamnopyranosyl group, and $R^{4'}$ represents an alkyl group having 1 to 6 carbon atoms.

Various acids conventionally used in alcoholysis can be used in the alcoholysis of soyasaponin B. Suitable examples of such acids include hydrogen halides such as hydrogen chloride, hydrogen bromide, etc., strong inorganic acids such as sulfuric acid, nitric acid, etc., strong organic acids such as trichloroacetic acid, trifluoroacetic acid, etc., Lewis acids such as aluminum chloride, boron trifluoride, titanium tetrachloride, titanium tetrabromide, etc.

The alcoholysis can preferably be conducted at about room temperature to about 150° C., more preferably about 50° to 100° C., for about 1 to about 6 hours.

The method of isolating the compounds represented by the formula (Ia) from the reaction mixture is not particularly limited and various known methods utilizing the physicochemical properties of the substances produced including those employed in separating soyasaponin B can be employed. Suitable examples of such methods include a method utilizing the differences in solubility between the products and impurities, a method utilizing the differences in adsorptive power and affinity for ordinary adsorbents such as activated carbon, XAD-2, silica gel, ion exchange resins, Sephadex, etc., a method utilizing the differences in the coefficient of distribution between two liquid phases, and a combination of such methods.

For example, the alcoholysate is mixed with water to form precipitates which are subjected to silica gel column chromatography and eluted stepwise with an eluant, e.g., a mixture of chloroform and ethanol to isolate each compound included in the formula (Ia).

The hydrolysis of the compound represented by the formula (Ia) can usually be carried out in an inert solvent in the presence of a catalyst under conditions employed conventionally in the hydrolysis of esters. Conventional catalysts can be used in this reaction. Suitable examples of catalyst which can be used include mineral acids such as hydrochloric acid, sulfuric acid, nitric acid, etc., inorganic basic compounds such as sodium hydroxide, potassium hydroxide, sodium carbonate, sodium hydrogen carbonate, potassium carbonate, potassium hydrogen carbonate, etc. Inorganic basic compounds are preferred as the catalyst.

Any conventional inert solvents can be used in the above reaction. Suitable examples of inert solvents include water, lower alcohols such as methanol, ethanol, propanol, etc., ethers such as dioxane, tetrahydrofuran, etc., dimethyl sulfoxide, dimethylformamide, etc., or a mixture thereof. The hydrolysis reaction can preferably be carried out at room temperature to 150° C., more preferably 50° to 110° C., for about 1 to about 6 hours.

The compound of the formula (Ib) can be isolated from the hydrolysate using isolation methods which are the same as or similar to those employed in the isolation of the compounds represented by the formula (Ia).

The compound of this invention represented by the formula (Ib) can be isolated from products of the partial hydrolysis of soyasaponin B in which hydrolysis is conducted in water or a mixture of water and one or more of the above-described solvents in the presence of hydrogen halides such as hydrogen chloride, hydrogen bromide, etc., strong inorganic acids such as sulfuric acid, nitric acid, etc., or strong organic acids such as trichloroacetic acid, trifluoroacetic acid, etc. The term "partial hydrolysis" used herein means hydrolysis in which no or substantially no splitting of aglycone of the starting saponin material occurs. The partial hydrolysis can usually be performed at room temperature to 150° C., preferably 50° to 110° C., for about 1 to about 6 hours.

The isolation of the compound represented by the formula (Ib) from the partial hydrolysate can be conducted using the above-described methods of isolation. For example, after extracting it with n-butanol to remove water-soluble components, the partial hydrolysate is subjected to silica gel column chromatography to separate it into respective components and the fraction corresponding to 3-0-($\beta$-D-glucuronopyranosyl)-soyasapogenol B is subjected to crystallization from a suitable solvent, e.g., a mixture of chloroform and acetone (1:1 by volume).

Representative examples of the compounds represented by the formula (I) include:
(1) 3-0-($\beta$-D-glucuronopyranosyl)-soyasapogenol B
(2) 3-0-[$\beta$-D-galactopyranosyl(1→2)-$\beta$-D-glucuronopyranosyl]-soyasapogenol B
(3) 3-0-[$\alpha$-L-arabinopyranosyl(1→2)-$\beta$-D-glucuronopyranosyl]-soyasapogenol B
(4) 3-0-[$\alpha$-L-rhamnopyranosyl(1→2)-$\beta$-D-galactopyranosyl(1→2)-$\beta$-D-glucuronopyranosyl]-soyasapogenol B
(5) 3-0-[$\alpha$-L-rhamnopyranosyl(1→2)-$\alpha$-L-arabinopyranosyl(1→2)-$\beta$-D-glucuronopyranosyl]-soyasapogenol B
(6) 3-0-(6-0-methyl-$\beta$-D-glucuronopyranosyl)-soyasapogenol B
(7) 3-0-(6-0-hexyl-$\beta$-D-glucuronopyranosyl)-soyasapogenol B
(8) 3-0-[$\beta$-D-galactopyranosyl(1→2)-(6-0-methyl-$\beta$-D-glucuronopyranosyl)]-soyasapogenol B
(9) 3-0-(6-0-ethyl-$\beta$-D-glucuronopyranosyl)-soyasapogenol B The compound of this invention thus-prepared can form salts with various pharmaceutically acceptable basic compounds. Of course, this invention includes within its scope such salts.

Suitable examples of the basic compounds which can be used for forming the above salts include inorganic basic compounds, for example, sodium hydroxide, potassium hydroxide, aluminum hydroxide, sodium carbonate, potassium carbonate, sodium hydrogen carbonate, etc., and organic basic compounds, for example, piperazine, morpholine, piperidine, ethylamine, dimethylamine, triethylamine, etc.

The compounds of the formula (I) can be used as a nephritis treating agent, and when used for this purpose are formulated into pharmaceutical compositions together with ordinary pharmaceutically acceptable carriers. Suitable carriers which can be used are, for example, diluents or excipients such as fillers, extenders, binders, wetting agents, disintegrants, surface active agents and lubricants which are usually employed to prepare such drugs depending on the dosage form.

Various dosage forms of the therapeutic agents as a nephritis treating agent can be selected according to the purpose of the therapy. Typical dosage forms which can be used are tablets, pills, powders, liquid preparations, suspensions, emulsions, granules, capsules, suppositories, and injectable preparations (solutions, emulsions, suspensions, etc.).

In molding a pharmaceutical composition containing the compounds of this invention as an active ingredient into a tablet form, a wide range of carriers known in the art can be used. Examples of suitable carriers include excipients such as lactose, white sugar, sodium chloride, glucose, urea, starch, calcium carbonate, kaolin, crystalline cellulose and silicic acid; binders such as water, ethanol, propanol, simple syrup, glucose, starch solution, gelatin solution, carboxymethyl cellulose, shellac, methyl cellulose, potassium phosphate and polyvinyl pyrrolidone; disintegrants such as dried starch, sodium alginate, agar powder, laminaria powder, sodium hydrogen carbonate, calcium carbonate, Tween, sodium lauryl sulfate, stearic acid monoglyceride, starch, and lactose; disintegration inhibitors such as white sugar, stearic acid glyceryl ester, cacao butter and hydrogenated oils; absorption promotors such as quaternary ammonium bases and sodium lauryl sulfate; humectants such as glycerol and starch; adsorbents such as starch, lactose, kaolin, bentonite and colloidal silicic acid; and lubricants such as purified talc, stearic acid salts, boric acid powder, Macrogol and solid polyethylene glycol.

In molding the pharmaceutical composition into a pill form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar. The tablets, if desired, can be coated, and made into sugar-coated tablets, gelatin-coated tablets, enteric-coated tablets, film-coated tablets, or tablets coated with two or more layers.

In molding the pharmaceutical composition into a suppository form, a wide variety of carriers known in the art can be used. Examples of suitable carriers include polyethylene glycol, cacao butter, higher alcohols, esters of higher alcohols, gelatin, and semi-synthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The amount of the compound of this invention as an active ingredient to be incorporated into a pharmaceutical composition useful as a nephritis treating agent is not particularly limited, and can vary over a wide range. A suitable therapeutically effective amount of the compound of the formula (I) used in this invention is usually about 1 to about 70% by weight, preferably 5 to 50% by weight, based on the entire composition.

There is no particular restriction on the manner of using the therapeutic agent as an anticomplementary agent, and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be administered intramuscularly, intracutaneously, subcutaneously, or intraperitoneally. The suppository is administered intrarectally.

The dosage of the nephritis treating agent is suitably selected according to the purpose of use, the symptoms, etc. Usually, a dosage of the compound of this invention is about 0.5 to about 20 mg/kg of body weight per day. The results of tests on the pharmacological effects of the compounds of the formula (I) serving as the active ingredient of the pharmaceutical compositions of this invention are shown below.

Pharmacological Testing

1. Compounds Tested

A. 3-0-($\beta$-D-glucuronopyranosyl)-soyasapogenol B
B. 3-0-[$\beta$-D-galactopyranosyl(1→2)-$\beta$-D-glucuronopyranosyl]-soyasapogenol B
C. 3-0-[$\alpha$-L-rhamnopyranosyl(1→2)-$\beta$-D-galactopyranosyl(1→2)-$\beta$-D-glucuronopyranosyl]-soyasapogenol B
D. 3-0-[$\alpha$-L-arabinopyranosyl(1→2)-$\beta$-D-glucuronopyranosyl]-soyasapogenol B
E. 3-0-[$\alpha$-L-rhamnopyranosyl(1→2)-$\alpha$-L-arabinopyranosyl(1→2)-$\beta$-D-glucuronopyranosyl]-soyasapogenol B
F. 3-0-(6-0-methyl-$\beta$-D-glucuronopyranosyl)-soyasapogenol B
G. Glycyrrhizin (comparison)

2. Anticomplementary Activity

The anticomplementary activity of the test compounds above was measured and confirmed by the testing method described in *Meneki Kagaku* (Immuno-Chemistry), Yuichi Yamamura et al., Ed. pages 830-834, Asakura Shoten, Tokyo, Japan (1973). Specifically, a test tube was charged with 0.5 ml of an aqueous dispersion of each of the test compounds, 0.5 ml of sensitized erythrocytes (EA) containing $1 \times 10^8$ cells/ml, 1 ml of a 5-fold diluted solution of a Veronal buffer solution containing isotonic gelatin (this 5-fold diluted solution is termed GVB++ for brevity), and 0.5 ml of complement serum (guinea pig complement) diluted 150 times with the GVB++. The mixture was maintained at 37° C. for 60 minutes. Then, 5 ml of an ice-cold physiological saline solution was added thereto, and the mixture was centrifuged. The absorbance of the supernatant separated was measured at $OD_{413}$, and the extent the test compound inhibited the hemolysis of the sensitized erythrocytes was determined. The 50% hemolysis inhibitory activity value ($\gamma$/ml) measured by the above method is shown in Table 1 below for each test compound.

TABLE 1

| Test Compound | Anticomplementary Activity ($\gamma$/ml) | |
|---|---|---|
| | Guinea Pig Complement | Human Complement |
| A | 5 | 5 |
| B | 1-2 | 5-10 |
| C | 125 | — |
| D | 3-5 | — |
| E | 100-150 | — |
| G | 500-1,000 | 500 |

As will be apparent from the result shown in Table 1, Test Compounds A to E which are used in the pharmaceutical compositions of this invention exhibited unexpectedly superior anticomplementary activity over Test Compound G (glycyrrhizin).

3. Inhibition of Forssman Reaction

The Forssman reaction discovered by Forssman in 1911 is based on the finding that rabbits immunized with the tissue of guinea pig and other animals produce antibodies capable of lysing sheep erythrocytes. This phenomenon means that the tissues of the guinea pig and other animals contain the same antigen as sheep erythrocytes. This antigen is called "Forssman antigen" and the corresponding antibody is called "Forssman antibody". The Forssman antigen is found in the tissues of man, guinea pigs, sheep, horses, cats, domestic fowls, tortoises, bacteria, etc., but is not found in rats, pigs, cows, rabbits, geese, pigeons, frogs. (J. Buchbinder, "Heterophile Phenomena in Immunology", *Review Arch. Pathol.*, 19, 841–880 (1935)).

Generally, the Forssman reaction is performed by immunizing an animal which does not have Forssman antigen such as rabbits, etc., with sheep erythrocytes as an antigen to obtain an antiserum (i.e., Forssman antibody) and intravenously injecting the antiserum into a guinea pig. The reaction is confirmed by the death of the guinea pig subjected to intravenous injection which occurs within a few minutes.

In other words, it can be said that the Forssman reaction is a cell-lytic lethal reaction (Allergy type II as defined by Gell & Coombs) which is caused by injecting the antibodies obtained from other animals immunized with Forssman antigen (glycolipids) present in cell surface or in the connective tissue into an animal which has a corresponding antigen (*Clinical Aspects of Immunology*, 3rd Ed., edited by P. G. H. Gell, R. R. A. Coombs and P. J. Lachmann, Blackwell Scientific Publications Osney Mead, Oxford, 85 Marylebone High Street London WIM 3 DE; Alicja B. Palczarska and Adolph P. Roszkowski "Inhibitors of Forssman Guinea Pig "Anaphylaxis"" in *Journal of Pharmacology and Experimental Therapeutics*, 185, No. 1 116-126 (1973)).

In Type II cell-lytic allergy, the complement system in the blood is activated accompanying the antigen-antibody reaction to release anaphylatoxin of C3a or C5a which leads to enhancement of the permeability of blood vessels. Particularly, in the Forssman reaction in guinea pig, transsude of blood components into alveoli of the lung causes blockage of the respiratory tract which leads to death of individual. (*J. Pharm. Exp. Ther.*, 185, No. 1 116-125 (1973)).

Therefore, inhibition of the formation of anaphylatoxin of C3a, C5a, etc., by anticomplementary agents enables one to survive even upon the administration of the Forssman antibody (hemolysin).

Method

Via a femoral vein, a guinea pig was administered 1 ml/kg of hemolysin (i.e., Forssman antibody anti-sheep heated stromata rabbit serum prepared in accordance with the method described in the aforementioned "Meneki Kagaku") followed immediately by administering test compounds dissolved in a 5% aqueous ethanol solution through another femoral vein. Survival rate 24 hours after the administration was scored and the results obtained are shown in Table 2 below.

TABLE 2

| Test Compound | Amount (mg/kg) | Survival/Total | Survival Rate (%) |
|---|---|---|---|
| A | 25 | 5/5 | 100 |
|   | 3 | 5/5 | 100 |
| F | 100 | 5/5 | 100 |
|   | 50 | 5/5 | 100 |
| G | 500 | 1/5 | 20 |
| Control | 5% Aqueous Ethanol Solution | 0/5 | 0 |

The test animals administered with a 5% aqueous ethanol solution (control lot) were all dead within 5 minutes.

As will be apparent from the results shown in Table 2 above, the compounds A and F of this invention exhibited superior inhibitory effects against the Forssman reaction over the Comparison Compound (glycyrrhizin).

It can be seen from the results shown in Tables 1 and 2 above that the compounds of this invention show an unexpectedly superior anticomplementary activity over Comparison Compound G (glycyrrhizin).

4. Therapeutic Effect on Nephrotoxin-Type Nephritis

Rat nephrotoxin ("NT" for brevity) was obtained as described below.

Rat Kidney cortex was homogenized with an equal quantity of physiological saline. The homogenized mixture was mixed with Freund's complete adjuvant (a product of Difco Company) in a volume ratio of 1:1. 2 ml of the resulting mixture was intramuscularly injected into a rabbit (body weight 3,100 g) to immunize the rabbit. A month and a half later, blood was taken from the heart of the rabbit and serum was obtained. The resulting serum was inactivated at 56° C. for 30 minutes, then salted out with a 40% saturated aqueous solution of ammonium sulfate, and fractionated. The γ-globulin (IgG) fraction was collected to obtain NT.

The therapeutic evaluation was carried out using male Wistar rats with a body weight of 150 to 160 g with three replications for each test compound. The test compound was intraperitoneally administered once every 24 hours for seven days. One hour after the administration of the test compound on the third day, the NT was applied. The NT was intravenously injected in an amount of 1 ml at a tail vein of each rat. Physiological saline solution was used as a control.

The proteinuria level (total amount excreted into the urine over a 24 hour period) was measured using turbidometry employing bovine serum albumin as a control by means of sulfosalicylic acid.

The results obtained are shown in Table 3 below.

TABLE 3

| | | Proteinuria Level (mg/day) Day Number | | | |
|---|---|---|---|---|---|
| Test Compound | | 1 | 4 | 7 | 10 |
| Control | 1 | 14 | 17 | 22 | 32 |
|  | 2 | 20 | 25 | 27 | 37 |
|  | 3 | 12 | 19 | 20 | 31 |
|  | Average | 15 | 20 | 23 | 33 |
| A | 1 | 1.9 | 1.2 | 0.9 | 7 |
| (3 mg/body) | 2 | 5.3 | 2.9 | 1.8 | 13 |
|  | 3 | 2.5 | 2.7 | 1.1 | 9 |
|  | Average | 3.2 | 2.3 | 1.3 | 9.7 |
| B | 1 | 2.4 | 1.9 | 3.1 | 11 |
| (3 mg/body) | 2 | 6.1 | 5.1 | 7.3 | 15 |
|  | 3 | 4.2 | 2.8 | 3.5 | 8 |
|  | Average | 4.2 | 3.3 | 4.6 | 11.3 |
| F | 1 | 5.8 | 4.6 | 6.2 | 9 |
| (3 mg/body) | 2 | 4.7 | 3.8 | 5.3 | 15 |
|  | 3 | 4.1 | 5.2 | 5.6 | 7 |
|  | Average | 4.9 | 4.5 | 5.7 | 10.3 |

The day number above is counted from the time of administration of the test compound which was 1 hour before the application of the NT.

The proteinuria level in a healthy rat is 0.5 to 5 mg/day. When the proteinuria level exceeds this range, especially when the proteinuria level is more than 10 mg/day, it may safely be said that nephritis has occurred. As can be seen from the results in Table 3, nephritis occurred in the control group, and in the case of the compounds of the present invention, the amount of proteinuria from the day of administration of NT to day 10 after administration is substantially the same as that of a healthy rat. Thus, the administration of the compounds of this invention can be seen to inhibit primary and secondary immune reactions.

5. Therapeutic Effects on Heymann-Type Nephritis

Male Wistar rats with a body weight of 180 to 200 g were used in the test. Rat kidney cortex was extracted, and homogenized with an equal quantity by volume of a physiological saline solution. The homogenate was centrifuged at 1,500 G for 1 hour. The supernatant liquid was purified in accordance with the method of T. S. Edgington et al., *Journal of Experimental Medicine*, 127, 555 (1968), and mixed with Freund's complete adjuvant 37 Ra (a product of Difco Company) in volume ratio of 0.4:1. The resulting mixture was injected intraperitoneally into isologous rats in an amount of 0.5 ml per rat. Then, the same amount of its mixture was administered every 2 weeks until the proteinuria level exceeded 100 mg/day. (This period was about 6 to 8 weeks.)

Each of the test compounds was intraperitoneally administered to the rats affected with Heymann-type nephritis (with a body weight of 300 to 350 g) once a day for 7 days, and then the amount of proteinuria (mg/day) was measured in the same manner as described above. Physiological saline solution was used as a control. The results obtained are shown in Table 4 below.

TABLE 4

| Test Compound | | Proteinuria Level (mg/day) | | | | | |
|---|---|---|---|---|---|---|---|
| | | Before Administration | Day Number | | | | |
| | | | 1 | 4 | 7 | 14 | 21 |
| Control | 1 | 132 | 127 | 135 | 126 | 135 | 114 |
| | 2 | 121 | 105 | 121 | 109 | 103 | 105 |
| | 3 | 135 | 117 | 137 | 132 | 121 | 109 |
| | Average | 129 | 116 | 131 | 122 | 119 | 109 |
| A | 1 | 117 | 89 | 42 | 27 | 3 | 8 |
| (3 mg/body) | 2 | 129 | 127 | 75 | 39 | 17 | 13 |
| | 3 | 123 | 119 | 58 | 18 | 9 | 7 |
| | Average | 123 | 112 | 58 | 28 | 3 | 9 |
| B | 1 | 151 | 152 | 121 | 46 | 29 | 20 |
| (3 mg/body) | 2 | 108 | 119 | 110 | 81 | 54 | 37 |
| | 3 | 124 | 108 | 105 | 65 | 31 | 29 |
| | Average | 128 | 126 | 112 | 64 | 38 | 29 |
| F | 1 | 162 | 154 | 132 | 72 | 32 | 13 |
| (10 mg/body) | 2 | 126 | 121 | 102 | 56 | 27 | 21 |
| | 3 | 137 | 141 | 115 | 82 | 43 | 26 |
| | Average | 142 | 139 | 116 | 70 | 34 | 20 |

Two to three weeks after the beginning of the testing, the body weights of the rats increased to 400 to 500 g, and normal proteinuria levels are believed to be 5 to 15 mg/day. As can be seen from the results in Table 4, the compounds of the present invention can cure Heymann-type nephritis.

6. Effects on Endotoxin Shock

Glycolipids in the cell wall of gram negative bacteria are known to serve as an endotoxin which causes endotoxin shock in many animals. Endotoxin shock is considered to be a model of disseminated intravascular coagulation ("D.I.C." for brevity) in humans.

Further, various reports support the view that a compound or agent showing an inhibitory effect on the Forssman reaction also exhibits a therapeutic effect on human D.I.C. (Abstracts of Proceedings of International Symposium on Quinines held on November 6 to 9, 1978, Tokyo).

Method

Each of Test Compound A and Predonisolone hemisuccinate (a product of Shionogi Seiyaku Co., Ltd.) dissolved in a 5% aqueous ethanol solution was administered intraperitoneally to a male mouse (dd strain) weighing 18 g. After 30 minutes 60 mg/kg of endotoxin isolated from *E. coli* K-12 strain according to the method described in *Carbohydrate Chemistry*, Vol. 15, p. 83 (1965), Academic Press was administered intravenously to the animal. The survival rate of the animal 24 hours after the administration of the endotoxin was scored. The results obtained are shown in Table 5 below.

TABLE 5

| Test Compound | Dose (mg/kg) | Survival Rate (%) |
|---|---|---|
| A | 50 | 78.3 |
| | 25 | 73.7 |
| | 12.5 | 50.0 |
| Predonisolone | 50 | 66.7 |

TABLE 5-continued

| Test Compound | Dose (mg/kg) | Survival Rate (%) |
|---|---|---|
| Hemisuccinate (comparison) | 25 | 86.7 |
| | 12.5 | 62.5 |
| Control | 5% Aqueous Ethanol Solution | 13.6 |

From the results shown in Table 5 above, it can be seen that most of the mice of the control group were dead within 24 hours of the administration of the endotoxin.

It can also be seen from the above results that the animals administered with the compounds of this invention showed apparently superior survival rate over the animals of control group and a survival rate of substantially the same level as the animals administered with Predonisolone succinate.

In view of the fact that the endotoxin has among various activities, a complement activating activity, the high survival rate achieved with the compound of this invention is considered to be due to its inhibitory effect on the activation of the complements.

7. Dose Response of Compound A in the Activation of Complements C1, C2 and C-EDTA (C3 to C9)

Dose Response for C1, C2 and C-EDTA was determined using EAC4, EAC14 or EAC142 cell. Each complement used in this test was obtained according to the method described in "Molecular Basis of Complement Action" 75-109 (1978) Meredith Corporation.

(i) Dose Response for C1

Using a microtiter board produced by Cooke Engineering Co., two fold serially diluted solutions of Compound A and C1 each diluted with GVB++ were prepared. The starting solution of Compound A used for the dilution was prepared by dissolving Compound A in a 5% aqueous ethanol solution (pH 7.5) to a concentration of 5,000 γ/ml. To respective holes of the microtiter board were added the following reagents (1) to (5) in this order.

(1) 1 drop of serially diluted Compound A in GVB++
(2) 1 drop of serially diluted C1 ($\times 1/20$ to $\times 1/1280$) in GVB++
(3) 1 drop of EAC4 cells ($1 \times 10^8$/ml) in GVB++
   (Incubated at 37° C. for 15 min. with vibration)
(4) 1 drop of C2 ($\times 1/10$) in GVB++
   (Incubated at 30° C. for 10 min. with vibration)
(5) 2 drops of 1/37.5 C-EDTA
   (Incubated at 37° C. for 60 min. with vibration followed by centrifugation)

The respective mixture were evaluated by the following standards:

| Degree | 0 | 1 | 2 | 3 | 4 |
|---|---|---|---|---|---|
| % Hemolysis | 0% | 25% | 50% | 75% | 100% |

The results obtained are shown in Table 6 below.

TABLE 6

| Dilution of C1 | Dilution of Compound A | | | | | | | | | Not Added | Not Added |
|---|---|---|---|---|---|---|---|---|---|---|---|
| | x2 | x4 | x8 | x16 | x32 | x64 | x128 | x256 | x512 | x1024 | |
| x20 | 4 | 4 | 4 | 4 | 4 | 4 | 4 | 4 | 4 | 4 | 4 | 4 |

TABLE 6-continued

| Dilution of C1 | Dilution of Compound A | | | | | | | | | | Not Added | Not Added |
|---|---|---|---|---|---|---|---|---|---|---|---|---|
| | x2 | x4 | x8 | x16 | x32 | x64 | x128 | x256 | x512 | x1024 | | |
| x40 | 3.5 | 3.5 | 3.5 | 3.5 | 4 | 4 | 4 | 4 | 4 | 4 | 4 | 4 |
| x80 | 2 | 2 | 2 | 2 | 2 | 4 | 4 | 4 | 4 | 4 | 4 | 4 |
| x160 | 0 | 0 | 0 | 0 | 1 | 3 | 4 | 4 | 4 | 4 | 4 | 4 |
| x320 | 0 | 0 | 0 | 0 | 0 | 2 | 4 | 4 | 4 | 4 | 4 | 4 |
| x640 | 0 | 0 | 0 | 0 | 0 | 2 | 4 | 4 | 4 | 4 | 4 | 4 |
| x1280 | 2 | 0 | 0 | 0 | 0 | 1 | 3 | 4 | 4 | 4 | 4 | 4 |
| Not Added | 2 | 0 | 0 | 0 | 0 | 0 | 0 | 0 | 0 | 0 | 0 | 0 |

(ii) Dose Response for C2

Serially diluted solutions of Compound A and C2 were prepared in the same procedure as the dose response for C1 except that C2 was used instead of C1. To respective holes of a microtiter board produced by Cooke Engineering Co. were added the following reagents (1) to (4) in this order.

(1) 1 drop of Compound A serially diluted with GVB++
(2) 1 drop of C2 serially diluted in GVB++
(3) 1 drop of EAC14 cells ($1 \times 10^8$/ml) in GVB++ (Incubated at 30° C. for 10 min.)
(4) 2 drops of 1/37.5 C-EDTA (Incubated at 37° C. for 60 min.)

The respective mixtures were evaluated in the same manner as in (i) above. The results obtained are shown in Table 7 below.

TABLE 7

| Dilution of C2 | Dilution of Compound A | | | | | | | | | | Not Added | Not Added |
|---|---|---|---|---|---|---|---|---|---|---|---|---|
| | x2 | x4 | x8 | x16 | x32 | x64 | x128 | x256 | x512 | x1024 | | |
| x40 | 4 | 4 | 4 | 4 | 4 | 4 | 4 | 4 | 4 | 4 | 4 | 4 |
| x80 | 4 | 3.5 | 3.5 | 3.5 | 3.5 | 3.5 | 3.5 | 3.5 | 3.5 | 3.5 | 3.5 | 3.5 |
| x160 | 4 | 3 | 3 | 3 | 3 | 3 | 3 | 3 | 3 | 3 | 3 | 3 |
| x320 | 4 | 2 | 2 | 2 | 2 | 2 | 2 | 2 | 2 | 2 | 2 | 2 |
| x640 | 4 | 1 | 1 | 1 | 1 | 1 | 1 | 1 | 1 | 1 | 1 | 1 |
| x1280 | 4 | 0.5 | 0.5 | 0.5 | 0.5 | 0.5 | 0.5 | 0.5 | 0.5 | 0.5 | 0.5 | 0.5 |
| x2560 | 4 | 0 | 0 | 0 | 0 | 0 | 0 | 0 | 0 | 0 | 0 | 0 |
| Not Added | 0 | 0 | 0 | 0 | 0 | 0 | 0 | 0 | 0 | 0 | 0 | 0 |

(iii) Dose Response for C-EDTA

Serially diluted solutions of Compound A and C-EDTA were prepared in the same manner as the dose response for C1 except that C-EDTA was used instead of C1. To respective holes of a microtiter board produced by Cooke Engineering Co. were added the following reagents (1) to (3) in this order.

(1) 1 drop of Compound A serially diluted in GVB++
(2) 2 drops of C-EDTA serially diluted in GVB++
(3) 2 drops of EAC142 cells ($5 \times 10^8$/ml in GVB++) (Incubated at 37° C. for 60 min. with vibration)

The respective mixtures were evaluated in the same manner as in (i) above. The results obtained are shown in Table 8 below.

TABLE 8

| Dilution of C-EDTA | Dilution of Compound A | | | | | | | | | | Not Added | Not Added |
|---|---|---|---|---|---|---|---|---|---|---|---|---|
| | x2 | x4 | x8 | x16 | x32 | x64 | x128 | x256 | x512 | x1024 | | |
| x20 | 4 | 4 | 4 | 4 | 4 | 4 | 4 | 4 | 4 | 4 | 4 | 4 |
| x40 | 4 | 3 | 3 | 3 | 3 | 3 | 3 | 3 | 3 | 3 | 3 | 3 |
| x80 | 4 | 2 | 2 | 2 | 2 | 2 | 2 | 2 | 2 | 2 | 2 | 2 |
| x160 | 4 | 2 | 2 | 2 | 2 | 2 | 2 | 2 | 2 | 2 | 2 | 2 |
| x320 | 4 | 1 | 1 | 1 | 1 | 1 | 1 | 1 | 1 | 1 | 1 | 1 |
| x640 | 4 | 0 | 0 | 0 | 0 | 0 | 0 | 0 | 0 | 0 | 0 | 0 |
| x1280 | 4 | 0 | 0 | 0 | 0 | 0 | 0 | 0 | 0 | 0 | 0 | 0 |
| Not Added | 4 | 0 | 0 | 0 | 0 | 0 | 0 | 0 | 0 | 0 | 0 | 0 |

From the results shown in Tables 6 to 8 above, it can be seen that Compound A showed a dose response to the inhibition of C1 activation on EAC4 cells but did not exhibit any dose response to the inhibition of C2 activation on EAC14 cells or C-EDTA (C3 to C9) activation on EAC142 cells. Although behavior of Compound A toward C4 remains to be clarified, it can safely be considered that Compound A inhibits C1 activation and exhibits an anticomplementary activity.

8. Acute Toxicity

The acute toxicity ($LD_{50}$ mg/kg) of the test compounds was determined on mice by intraperitoneal administration in the case of Compounds A to F and by intravenous administration in the case of Compound G. The results obtained are shown in Table 9 below.

TABLE 9

| Test Compound | Acute Toxicity $LD_{50}$ (mg/kg) |
|---|---|
| A | >300 |

TABLE 9-continued

| Test Compound | Acute Toxicity LD$_{50}$ (mg/kg) |
|---|---|
| B | >300 |
| C | >300 |
| D | >300 |
| E | >300 |
| F | >300 |
| G | >300 |

This invention will be explained in greater detail hereinbelow with reference to the following Reference Examples and Examples.

REFERENCE EXAMPLE 1

(a) Soyasaponin B (500 mg) was dissolved in 30 ml of methanol. After adding 1.5 ml of a 15 N sulfuric acid, the solution was refluxed for 3.5 hours. Cold water was added to the reaction mixture to form precipitates which were collected and washed with water sufficiently. The precipitates were absorbed on a silica gel column and developed with a mixture of chloroform-ethanol in turn (20:1 by volume 200 ml; 10:1 by volume 150 ml; 5:1 by volume 200 ml; and 2:1 by volume 200 ml in this order) and the following compounds were recovered from a portion of the respective eluant fractions.

| Eluant Fraction (CHCl$_3$—C$_2$H$_5$OH vol/vol.) | Compound Recovered |
|---|---|
| 20:1 | 3-0-(6-0-methyl-$\beta$-D-glucurono pyranosyl)-soyasapogenol B (71 mg) (Melting Point: 249–250° C.) |
| 10:1 | 3-0-[$\beta$-D-galactopyranosyl(1 → 2)-(6-0-methyl-$\beta$-D-glucuronopyranosyl)]-soyasapogenol B (Melting Point: 262–263° C.) and 3-0-[$\alpha$-L-arabino-pyranosyl(1 → 2)-(6-0-methyl-$\beta$-D-glucurono-pyranosyl)]-soyasapogenol B (Melting Point: 260–265° C.) |
| 5:1 | 3-0-[$\alpha$-L-rhamnopyranosyl(1 → 2)-$\beta$-D-galactopyranosyl(1 → 2)-(6-0-methyl-$\beta$-D-glucuronopyranosyl)]-soyasapogenol B (Melting point: 270–274° C.) |

3-0-(6-O-methyl-$\beta$-D-glucuronopyranosyl)-soyasapogenol B (71 mg) thus-obtained was dissolved in 2 ml of methanol and 2 ml of a 1 N aqueous NaOH solution was added to the solution, followed by refluxing for 2 hours. After the reaction mixture was mixed with cold water and the pH value adjusted to about 1 with a 1 N aqueous HCl solution, it was extracted with n-butanol. The n-butanol fraction was concentrated to dryness under reduced pressure. Crystallization of the residue from a mixture of chloroform-acetone (1:1 by volume) afforded 50 mg of 3-0-($\beta$-D-glucuronopyranosyl)-soyasapogenol B.

Melting Point: 231°–232° C. (decomposition).
Elemental Analysis for C$_{36}$H$_{58}$O$_9$:

|  | C | H |
|---|---|---|
| Calculated (%): | 68.11 | 9.21 |
| Found (%): | 67.85 | 9.08 |

Silica Gel Thin Layer Chromatography Using "Kiesel Gel F$_{254}$" (a trade name for a product of Merck Co.).

1. Chloroform-Methanol-Water (65:35:8 by volume) R$_f$=0.38
2. Isopropanol-2 N Aqueous Ammonia Solution (100:15 by volume) R$_f$=0.21

Solubility: Very soluble in methanol, ethanol, n-propanol, n-butanol, aqueous alkali solution, pyridine, dimethyl sulfoxide and dimethylformamide; soluble in acetone, ethyl acetate and methyl ethyl ketone; and sparingly soluble in benzene, chloroform, diethyl ether, n-hexane and petroleum ether.

(b) Soyasaponin B (500 mg) was dissolved in 30 ml of ethanol saturated with hydrogen chloride and the solution was refluxed for 3 hours. Cold water was added to the reaction mixture to form precipitates which were collected and washed with water. The precipitates were then purified through a silica gel column chromatography (eluant: chloroform-ethanol (20:1 by volume (200 ml), 10:1 by volume (150 ml), 5:1 by volume (200 ml) and 2:1 by volume (200 ml) in this order) and the following compounds were recovered from a portion of respective eluant fractions.

| Eluant Fraction (CHCl$_3$-C$_2$H$_5$OH vol./vol.) | Compound Recovered |
|---|---|
| 20:1 | 3-0-(6-0-ethyl-$\beta$-D-glucurono-pyranosyl)-soyasapogenol B (75 mg) |
| 10:1 | 3-0-[$\beta$-D-galactopyranosyl(1 → 2)-(6-0-ethyl-$\beta$-D-glucuronopyranosyl)]-soyasapogenol B and 3-0-[$\alpha$-L-arabinopyranosyl(1 → 2)-(6-0-ethyl-$\beta$-D-glucuronopyranosyl)]-soyasapogenol B |
| 5:1 | 3-0-[$\alpha$-L-rhamnopyranosyl(1 → 2)-$\beta$-D-galactopyranosyl(1 → 2)-(6-0-ethyl-$\beta$-D-glucuronopyranosyl)]-soyasapogenol B |

3-0-(6-O-ethyl-$\beta$-D-glucuronopyranosyl)-soyasapogenol B (75 mg) thus-obtained was dissolved in 2 ml of ethanol and 2 ml of a 1 N aqueous KOH solution and the mixture was refluxed for 2 hours. The reaction mixture was mixed with cold water and the pH value adjusted to about 1 with a 1 N aqueous HCl solution followed by extraction with n-butanol. The n-butanol fraction was concentrated to dryness under reduced pressure and crystallization of the residue from a mixture of chloroform-acetone (1:1 by volume) afforded 45 mg of 3-0-($\beta$-D-glucuronopyranosyl)-soyasapogenol B.

Melting Point: 231°–232° C. (decomposition).

REFERENCE EXAMPLE 2

Soyasaponin (1 g) was dissolved in 70 ml of distilled water and the solution was mixed with 5 ml of a 15 N aqueous sulfuric acid solution followed by refluxing for 2.5 hours. The reaction mixture was extracted with n-butanol. The n-butanol fraction was concentrated to dryness under reduced pressure. The residue was adsorbed on a silica gel column and developed with a mixture of chloroform-ethanol (20:1, 10:1, 5:1 and 2:1 by volume) to obtain 350 mg of 3-0-($\beta$-D-glucuronopyranosyl)-soyasapogenol B.

Melting Point: 231°–232° C. (decomposition).

EXAMPLE 1

| Sodium Salt of the Compound A of the Invention | 500 mg |
|---|---|
| Glucose | 250 mg |

| | |
|---|---|
| Distilled Water for Injection | to make the total amount 5 ml |

The sodium salt and glucose were dissolved in distilled water for injection, and the solution was poured into a 5 ml ampoule. The air was purged with nitrogen, and the ampoule was heated at 121° C. for 15 minutes to sterilize the solution to obtain an injectable preparation.

EXAMPLE 2

| | |
|---|---|
| Compound B of the Invention | 500 mg |
| Semi-Synthetic Glyceride Base | to make the total amount 2,000 mg |

Compound of the invention was added to the semi-synthetic glyceride base, and they were mixed and suspended at 50° C. The mixture was cast into a mold, and allowed to cool naturally. The product was removed, and thus, a suppository was obtained.

EXAMPLE 3

| | |
|---|---|
| Compound B of the Invention | 150 g |
| Avicel (trademark for a product of Asahi Kasei Kabushiki Kaisha) | 40 g |
| Corn Starch | 30 g |
| Magnesium Stearate | 2 g |
| TC-5 (trademark for hydroxypropyl-methyl cellulose) | 10 g |
| Polyethylene Glycol | 3 g |
| Castor Oil | 40 g |
| Methanol | 40 g |

Compound B of this invention, the Avicel, the corn starch and the magnesium stearate were mixed and ground, and then tableted using a conventional pounder (R 10 mm) for sugar coating. The resulting tablets were coated with a film coating agent composed of TC-5, polyethylene glycol 6000, castor oil and methanol to produce film-coated tablets.

While the invention has been described in detail and with reference to specific embodiments thereof, it will be apparent to one skilled in the art that various changes and modifications can be made therein without departing from the spirit and scope thereof.

What is claimed is:

1. A method for treating nephritis, which comprises administering an antinephritic pharmaceutical composition comprising (a) an antinephritic therapeutically effective amount of at least one soyasapogenol B compound represented by the general formula (I):

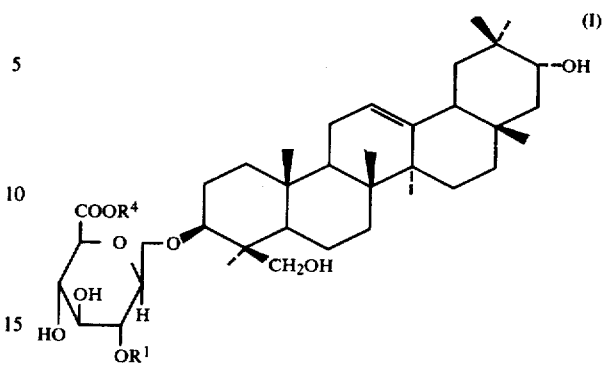

wherein $R^1$ represents a hydrogen atom or a group represented by the formula:

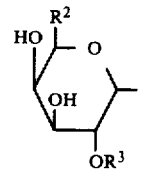

wherein $R^2$ represents a hydrogen atom or a hydroxymethyl group, $R^3$ represents a hydrogen atom or a rhamnopyranosyl group, and $R^4$ represents a hydrogen atom or an alkyl group having 1 to 6 carbon atom, with the proviso that $R^1$ and $R^4$ are not simultaneously hydrogen atoms, or pharmaceutically acceptable salts thereof and a pharmaceutically acceptable carrier, to a nephritic patient in a daily dose of about 0.5 to about 20 mg/kg of body weight per day.

2. A method for inhibiting the complement system in a body fluid which comprises subjecting said fluid to the action of an effective complement inhibiting amount of a compound represented by the general formula (I):

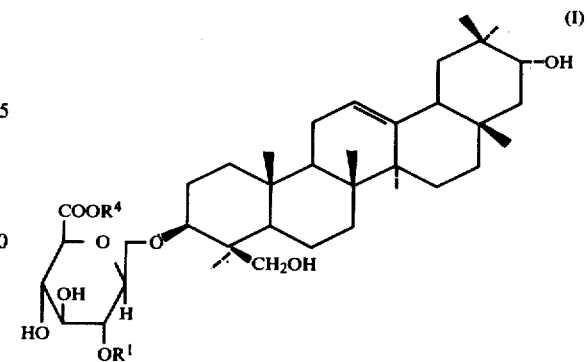

wherein $R^1$ represents a hydrogen atom or a group represented by the formula:

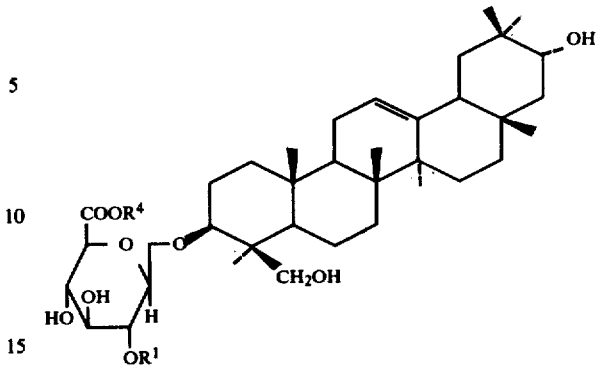

wherein $R^1$ represents a hydrogen atom or a group represented by the formula:

wherein $R^2$ represents a hydrogen atom or a hydroxymethyl group, $R^3$ represents a hydrogen or a rhamnopyranosyl group, and $R^4$ represents a hydrogen atom or an alkyl group having 1 to 6 carbon atoms, or pharmaceutically acceptable salts thereof.

5. The method according to claim 4 wherein the compound is administered intravenously.

6. A method as claimed in any of claims 2 to 5, wherein said compound is 3-0-(β-D-glucuronopyranosyl)-soyasapogenol B.

7. A method as claimed in any of claims 1 to 5, wherein said compound is 3-0-[β-D-galactopyranosyl-(1→2)-β-D-glucuronopyranosyl]-soyasapogenol B.

* * * * *

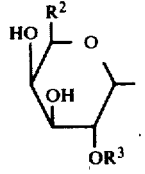

wherein $R^2$ represents a hydrogen atom or a hydroxymethyl group, $R^3$ represents a hydrogen or a rhamnopyranosyl group, and $R^4$ represents a hydrogen atom or an alkyl group having 1 to 6 carbon atoms, or pharmaceutically acceptable salts thereof.

3. The method according to claim 2 wherein the body fluid is blood serum.

4. A method for inhibiting the complement system in a warm blooded animal which comprises internally administering to said animal an effective complement inhibiting amount of a compound represented by the general formula (I):